(12) United States Patent
Cole et al.

(10) Patent No.: US 10,600,626 B1
(45) Date of Patent: Mar. 24, 2020

(54) MASS CALIBRATION DEVICE FOR A MASS SPECTROMETER

(71) Applicant: Thermo Finnigan LLC, San Jose, CA (US)

(72) Inventors: Jason S. Cole, Austin, TX (US); Edward B. McCauley, Cedar Park, TX (US)

(73) Assignee: THERMOS FINNIGAN LLC, San Jose, CA (US)

( * ) Notice: Subject to any disclaimer, the term of this patent is extended or adjusted under 35 U.S.C. 154(b) by 0 days.

(21) Appl. No.: 16/220,291

(22) Filed: Dec. 14, 2018

(51) Int. Cl.
- *H01J 49/00* (2006.01)
- *G01N 33/00* (2006.01)
- *H01J 49/16* (2006.01)
- *H01J 49/26* (2006.01)

(52) U.S. Cl.
CPC ...... *H01J 49/0027* (2013.01); *G01N 33/0006* (2013.01); *H01J 49/0009* (2013.01); *H01J 49/168* (2013.01); *H01J 49/26* (2013.01)

(58) Field of Classification Search
CPC .. H01J 49/0027; H01J 49/0009; H01J 49/168; H01J 49/26; G01N 33/0006
USPC ................................ 250/281, 282, 284, 288
See application file for complete search history.

(56) References Cited

U.S. PATENT DOCUMENTS

| | | | |
|---|---|---|---|
| 5,703,360 A | 12/1997 | Fischer et al. | |
| 6,635,885 B2 | 10/2003 | McCauley et al. | |
| 7,737,395 B2 | 6/2010 | Goodley et al. | |
| 8,829,430 B2 | 9/2014 | Ledford, Jr. | |
| 8,975,573 B2 | 3/2015 | Rafferty et al. | |
| 2010/0223979 A1* | 9/2010 | Ploehn | G01N 15/0826 73/38 |
| 2012/0227461 A1 | 9/2012 | Lee et al. | |

OTHER PUBLICATIONS

Ellefson et al., "Calibration of mass spectrometers for quantitative gas mixture analysis", Journal of Vacuum Science & Technology A 5 (1987), pp. 134-139.
Stout et al., "Tuning and Calibration in Thermospray LiquidChromatography/Mass Spectrometry Using Perfluorinated Alkyl Acids and Their Ammonium Salts", Organic Mass Spectrometry, vol. 25, 1990, pp. 187-190.
Williams, "Mass spectrometric analysis of volatiles in fluid inclusions:aliquot calibration valve to simulate inclusion rupture", Chemical Geology 131 (1996), pp. 155-165.

* cited by examiner

*Primary Examiner* — Nicole M Ippolito
*Assistant Examiner* — Hanway Chang
(74) *Attorney, Agent, or Firm* — David A. Schell; Nicholas Cairns

(57) ABSTRACT

A calibration device and a method of calibrating a mass spectrometer are described where two or more immiscible mass spectrometry calibration compounds in close proximity to each other share a common headspace volume above their liquid surfaces. This arrangement allows each calibrant to evaporate at differing rates while allowing the headspace concentrations to remain relatively unchanged over time (forming a quasi-equilibrium calibrant mixture). The mixture is either delivered to an ion source of a mass spectrometer or to a vacuum pump via a flow restrictor from a calibration vial. The calibrant gas mixture in the headspace volume may be used to calibrate a mass spectrometer.

14 Claims, 7 Drawing Sheets

MASS CALIBRATION DEVICE FOR A MASS SPECTROMETER

TECHNICAL FIELD

This invention relates generally to an apparatus and methods concerning calibration of a mass spectrometer, and more specifically to calibration of a mass spectrometer used with a gas chromatograph.

BACKGROUND

Calibration methods for gas chromatograph-mass spectrometers (GC-MS) typically employ a fluorinated calibrant. This calibrant is generally used both as a mass calibrant to properly assign ion masses, and as a resolution calibrant to adjust for proper mass peak widths when tuning quadrupole based mass spectrometers. The fluorinated compound selected may include high or low boiling perfluorokerosene, perfluorotributylamine (FC-43), perfluorotripentylamine (FC-70) or similar calibrants. Perfluorinated mass calibrants are generally preferred due to the monoisotopic nature of fluorine, the negative mass defect of resulting ions, and the ability of these classes of mixtures and compounds to exist as a liquid at room temperature while also having a high molecular weight. This allows a simple vapor based introduction of a high mass calibrant from a headspace of a calibration vial at ambient temperature without the need for heating the calibrant vial and associated delivery hardware.

While suitable for general electron ionization (EI) and positive chemical ionization (PCI) over a wide mass range, the above calibrants suffer in negative ion chemical ionization (NCI) due to low ion abundance below about mass to charge ratio (m/z) 150 daltons (Da). Low ion abundances in this region are due to the very low energy transfer of the NCI ionization process which precludes significant fragmentation of parent molecules. This presents problems when accurate mass calibration or resolution calibration is needed at lower masses, as accurate mass axis calibration and peak resolution calibration are very difficult if not impossible with poor ion abundances.

A calibrant such as perfluorotributylamine may contain a mixture of positional isomers due to perfluorinated n-butyl, sec-butyl, iso-butyl and tert-butyl groups. Even these isomers have very similar vapor pressures, identical molecular mass and quite similar fragmentation patterns. Identical mass and similar vapor pressure and fragmentation pathway allows long term usage without observable change over time in mass spectral peak abundances. Peak abundances which do not change over time is considered an advantage for repeatable instrument calibration as well as customer perception. The disadvantage of using isomeric mixtures or single compounds for mass calibration is that ion diversity is limited by the fragmentation pathway of a single molecular weight. For NCI operation wherein fragmentation is largely limited, a single molecular weight calibrant limits ion diversity and low mass ion intensity even further. By contrast, calibrant mixtures are known such as high and low molecular weight perfluorokerosene which contain a range of fluorocarbons having similar chemistry but differing mass. This offers the ability for an extended range of mass calibration for NCI (particularly at high mass), but low mass ion intensity of these mixtures is generally low due to the low mole fraction of low molecular weight fluorocarbons. Mixtures of these types can also suffer from long term shifts in ion abundances due the changing headspace concentration of differing molecular weight species.

Traditional methods of introducing calibration compounds, e.g., perfluorotributylamine to the ionization region of mass spectrometers often involve intermediate use of ball valves or needle valves or similar gate devices between a source of calibrant vapor and an ion source of a mass spectrometer. Alternatively, calibrants may be delivered indirectly to the ion source of the mass spectrometer by flooding the vacuum chamber with a pre-evacuated vial containing such compounds. Instrument designs which feed the calibrant directly to the ion source of the mass spectrometer typically utilize needle valves due to the extremely small quantities (<4 ng/s) of calibrant required for effective instrument calibration. These valves may be expensive due to close machining tolerances involved in their production.

Different quantities of calibrants may be necessary based on whether an instrument is operating in electron ionization (EI), positive ion chemical ionization (PCI), or negative ion chemical ionization (NCI) modes of operation. Other difficulties arising from such metering methods may include: poor regulation due to variations in headspace pressure, poor regulation due to self-contamination (for example, from outgas sing of adsorbed calibrant from O-rings, valve seats, ceramics and internal packings), lack of reproducibility when returning a valve to a previous setting, inaccurate or unknown volume delivery and poor equilibrium time.

U.S. Pat. No. 7,737,395 describes a mass calibration formulation using a mass calibrant along with a "moderator substance" having a lower vapor pressure than the mass calibrant. The mass calibrant (0.1%-10% composition in the mixture) may comprise FC-70 or other low vapor pressure chemistries suitable for damping the intensity of the calibrant ions. The moderator may also serve to generate calibration ions and may include common mass spectrometry calibrants such as, fluorinated polyphenylethers, polyfluoroalkyls, polysilicones, triperfluoroalkylamines, etc. A potential feature of the above methodology is that high vapor pressure fluids (generally lower molecular weight) which might yield intense lower calibration masses can be dampened in accordance with their concentration in the moderator. The vapor pressure of any given compound in an ideal mixture can be expressed in accordance with Raoult's law. Raoult's law states that the partial vapor pressure of each component of an ideal mixture of liquids is equal to the vapor pressure of the pure component multiplied by its mole fraction in the mixture. Calibrants which approach the theory of Raoult's law may be expected to have similar chemistries e.g. FC-43 and FC-70 which are both triperfluoroalkylamines.

Mass calibrants have also been introduced specifically for chemical ionization (CI) operation which can extend to lower masses. One such material is PFDTD (perfluorodimethyltrioxadodecane). PFDTD can offer advantages for negative ion mass calibration as it covers a lower mass range compared to FC-43. The minimum useful mass for FC-43 in NCI mode is generally m/z 283 Da. Even so, it represents only about 5% relative abundance compared to the next higher mass of m/z 452. By contrast, PFDTD offers intense ions at m/z 185, 351 and 449 for methane NCI. While this calibrant extends calibration to lower masses relative to FC-43, even lower mass calibration is desirable.

The use of PFDTD generally is reserved for CI calibration (PCI and NCI inclusive) using additional metering hardware. The need for additional hardware arises from the fact that CI operation is carried out at elevated ion source pressures in order to favor ion-molecule reactions between reagent ions and neutral analyte molecules. This requires metering the calibrant directly into the ion source rather than delivering it into the vacuum manifold as is often done with FC-43 during EI calibration. This additional hardware results in higher manufacturing costs.

A significant drawback of the mixture approach as described in U.S. Pat. No. 7,737,395 is the inherent time varying intensity of each calibrant represented in the vial headspace. The concentrations of each calibrant will vary over time unless the evaporation of the mixture constitutes the behavior of an azeotrope. In addition, it is unlikely that a real mixture of calibrants would adhere to Raoult's law, which would be necessary if the mixture were to lend itself to a predictable change in concentration over time. While mass spectrometers can calibrate over a wide range in ion intensities, it is more desirable to have a consistent mass spectrum which remains unchanged over the course of many weeks than it is to have mass peaks which initially have a given intensity and then change over time. Such changes could imply for example a mass-dependent roll-off in instrument response rather than a change in composition of the calibrant.

U.S. Pat. No. 6,635,885 describes an apparatus designed to provide a continuously regenerated quasi-equilibrated calibrant vapor to the ion source of a mass spectrometer. The design of this invention is such that the calibration gas is always in an "on" state, being delivered either to a mass spectrometer ion source or to a roughing vacuum pump. This allows the vapor to be in a state of perpetual equilibrium with surfaces at all times such that a rapid and stable response is achieved when a calibration source is required for EI or CI modes of operation. Very low concentrations of vapors in the gas phase can be subject to adsorption and desorption effects on active surfaces of plumbing and valve components resulting in poor reproducibility and response times. U.S. Pat. No. 6,635,885 largely eliminates these ill effects. Against the above background there is need for an improved multi-calibrant, time-stable, extended range mass calibration apparatus and method.

SUMMARY

The invention described herein comprises a calibration device and a method whereby two or more mostly immiscible calibration compounds (for example, two liquids that form two separate layers when mixed or shaken together under ambient conditions) are separated in a common receptacle but remain open to a common headspace above their liquid surfaces. This allows pure or near pure calibrants to deliver their respective vapors into the headspace without an attenuation effect when using a moderator substance of the mixture approach as described in U.S. Pat. No. 7,737,395. This arrangement allows each calibrant to evaporate at differing rates while allowing the headspace concentrations to remain relatively unchanged over time (quasi-equilibrium). A calibrant gas mixture in a vial headspace may therefore be continuously equilibrated when the mass spectrometer is in operation and under vacuum.

A gas delivery apparatus is described for delivering a calibrant gas mixture to an ionization chamber of a mass spectrometer evacuated by a vacuum pump. Mass spectrometers are required to operate at relatively high vacuum mainly to facilitate gaseous ion transport. The majority of currently available mass spectrometers are evacuated in at least two vacuum stages. The first stage comprises an external roughing mechanical vacuum pump coupled with a second stage high vacuum turbomolecular vacuum pump that is usually housed within a mass spectrometer. The gas delivery apparatus includes a plurality of separated immiscible liquid calibrants contained in a common receptacle, such as a small vial with two partitioned sections. The calibration vial may have a total volume of about 0.1 to 5.0 mL, preferably about 0.5 to 3 mL.

A gating means may be used to transport a quasi-equilibrium calibrant vapor mixture containing a permanent inert gas either to the ion source of a mass spectrometer or to waste via a vacuum pump or other vacuum source thereby maintaining a constant flow of the calibrant gas either to the ionization chamber or to the vacuum pump. Permanent inert gases may comprise air (which may include or not include water vapor), nitrogen, argon, helium or mixtures of these gases thereof. Calibrant vapor may be introduced into an ion source of a mass spectrometer or routed to waste by a gate means. A valve or any other device or mechanism that allows calibrant vapor to be routed to two different pathways either exclusively via one pathway or just split between the two pathways may be used. For example, by using a multiport valve combined with capillary flow restrictors as described in U.S. Pat. No. 6,635,885. The flow restrictors may have a preselected internal diameter and length for delivery of calibrant gas at a desired flow rate. A calibrant receptacle or vial may have a venting flow restrictor which may be vented to outside air, dried air, or any inert gas such as nitrogen, helium, or argon.

Instead of one internally partitioned calibration vial or receptacle, two or more calibration vials may be used instead, wherein each calibration vial holds at least one liquid calibrant and wherein all of the calibration vials have a common headspace or a common headspace volume where their vapors may combine before being introduced into an ionization chamber of a mass spectrometer. For example, a headspace volume of separate vials may be exist that is connected to each vial by appropriate tubing or two. Another example may involve two or more separate vials being placed in a common container, wherein the container provides a common headspace. One skilled in the art would recognize that many permutations involving many different types of vessels may be used to contain liquid calibrants and to provide the calibrants with a common headspace volume.

Calibrants may contain at least one triperfluoroalkyl group or at least one perfluoroalkyl group. A ratio of calibrant gas vapors in the headspace may be periodically monitored, whereby any significant change in the ratio over time may indicate that at least one of the liquid calibrants may need to be replenished.

DETAILED DESCRIPTION

Definitions. The term "vapor" as used herein refers to a gaseous volume or body of gas resulting from an evaporated liquid. The terms gas and vapor are used interchangeably herein. The terms calibration gas or calibration vapor refer to evaporated liquids which may include a permanent relatively inert gas or gasses (inert to the calibrants) entrained with the evaporated liquid. The terms calibrant, mass calibrant and calibration compound as used herein refer to either a liquid form of such a calibrant(s) or refer to a vapor form of such a calibrant. The term, "inert" as used herein when referring to inert materials means relatively inert both physically and chemically with respect other components in the apparatus. The term "about" as used herein in conjunction with numerical values or ranges conveys a tolerance variance from the numerical value or range that one skilled in the art would recognize as being consistent with an intended function reliant on the numerical value or range. The term "quasi equilibrated" refers to a steady state condition of near equilibrium wherein gas phase concentrations of mass calibrants approach that of a closed system. The term vial or calibration vial as used herein refers to a receptacle for holding an appropriate amount of at least one liquid calibrant. The term headspace as used herein refers to any space within a calibration vial that is not taken up by vial structure, calibrant or any porous calibrant holder. Vials may have internal partitions for holding at least two calibrants. Separate vials containing at least one liquid calibrant in each vial, may be placed in a common vial holder or receptacle wherein the vial holder provides a common headspace volume.

Figure 1:
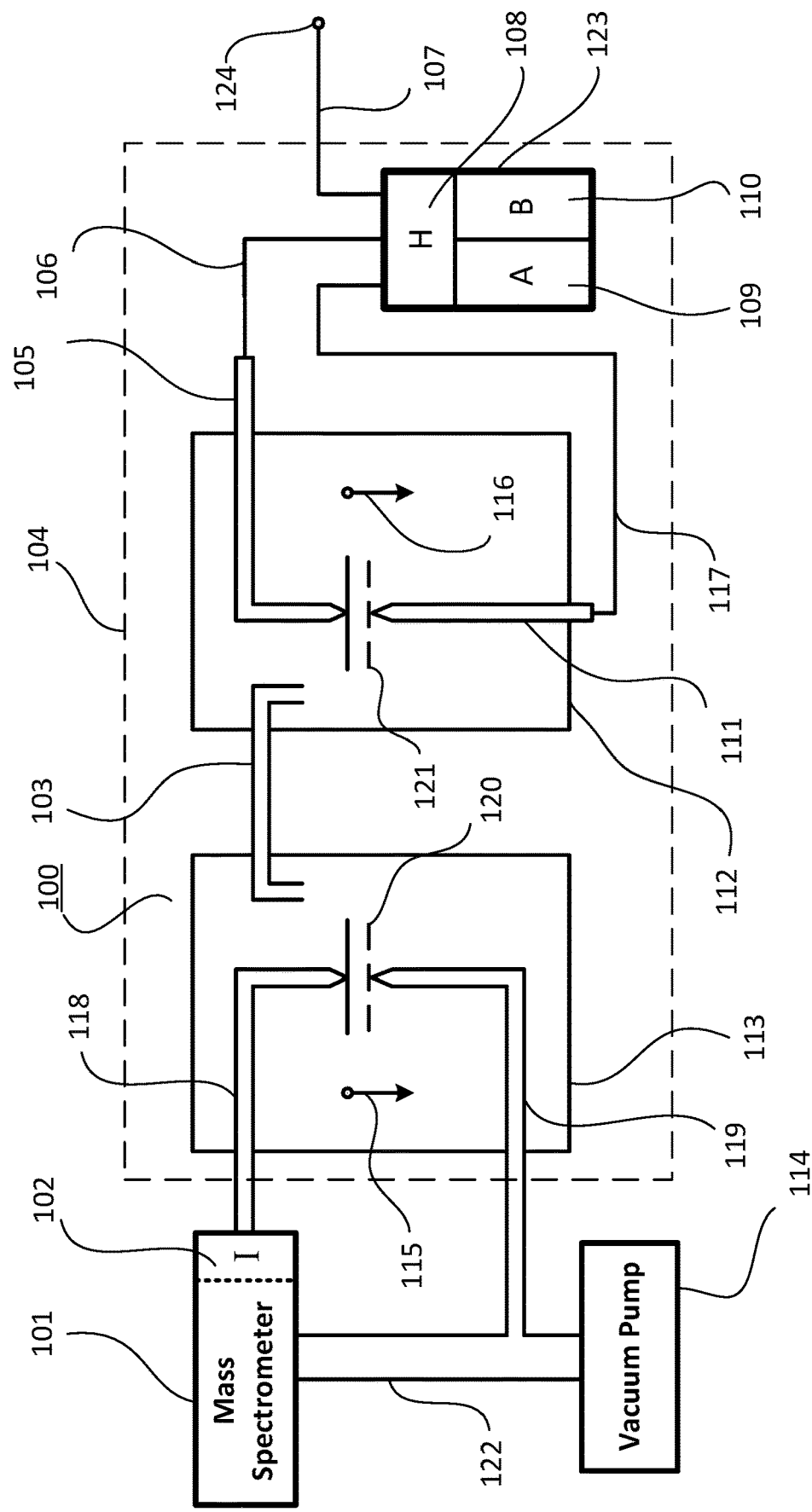
FIG. 1 shows a mass calibration apparatus having two calibrants, two metering restrictors and two 3-way valves.

Referring to FIG. 1, an example is shown of an embodiment of methods described herein which uses two metering restrictors 106 and 117 and two 3-way valves, 112 and 113. A calibrant gas delivery apparatus 104 is shown connected with an ionization source (I) 102 of a mass spectrometer which is maintained at low pressure by a high vacuum pump, for example, a turbo-molecular pump (not shown) which is backed by a suitable backing vacuum roughing mechanical pump 114. Roughing vacuum pumps for GC-MS instruments may operate in the range of about 0.5 to 6 cubic feet per minute (cfm). Examples of suitable GC-MS vacuum roughing pumps include oil-based vacuum pumps of the rotary vane type or rotary scroll "tip seal" vacuum pumps. The calibration delivery apparatus includes a calibration vial 123 which holds a calibration gas mixture in a headspace volume (H) 108 inside the vial. In operation, the headspace volume 108 holds a quasi-equilibrated gas-vapor mixture comprising vapor calibrants from liquids (A) 109 and liquid (B) 110 that are contained separately inside vial 123.

Liquids A and B may be selected to be immiscible fluids, and most preferably may be highly insoluble in each other. By selecting fluids which have a low and limited solubility in each other, fluid A cannot act as a moderator for fluid B, and fluid B cannot act as a moderator for fluid A. The headspace concentration of A is substantially independent of the presence of B, while the headspace concentration of B is substantially independent of the presence of A. A venting capillary tube 107 serves to vent the headspace volume 108 to atmosphere, or to an inert gas source connected to or flowing past an inlet end 124 of the venting capillary 107.

The purpose of the venting capillary is to allow the headspace of the vial to remain substantially at atmospheric pressure without undue loss of calibrant vapor to atmosphere by diffusion. The flow rate of venting gas through the vent capillary is preferably below about 0.05 mL/min. This low flow into and out of the calibrant vial headspace ensures that headspace concentrations of calibrants remain near that of a closed system, e.g. if the calibrant(s) were in a closed vial at the same temperature.

Two calibrant gas capillary tube flow restrictors 106 and 117 are connected to the headspace volume 108. The capillary tubes 106 and 117 serve to allow different amounts of calibrant vapor to enter the mass spectrometer ion source by having different diameters and/or different lengths of capillary tubing. Both the lengths and the diameters of capillary tubing 106 and 117 are selected to allow for appropriate different respective flow rates of a calibrant gas mixture into the ion source 102 for mass spectrometry calibration requirements.

The flow rate is primarily dependent upon the internal diameter and length of the capillary restrictors, the permanent gas type which entrains the calibrant vapors, and the pressure drop. The flow rate through the capillary restrictors 106 and 117 is not significantly affected by the vacuum pressure in an operable evacuated ionization chamber of a mass spectrometer or when diverted to an operable roughing vacuum pump of a mass spectrometer. That is, whether the pressure is $10^{-3}$ Torr or whether it is $10^{-8}$ Torr, the flow rate is about the same with both vacuum pressures being acceptable. Naturally, $10^{-8}$ Torr would be expected to pull a little more calibrant vapor than would $10^{-3}$ Torr but not significantly more to affect the pseudo-equilibrium.

A capillary tube having a 0.025 mm internal diameter and 40 cm long may be used for calibrant gas capillary tube flow restrictor 117 with the mass spectrometer operating in electron ionization mode. A 0.050 mm internal diameter and 65 cm long capillary tubing may be used for a second calibrant gas capillary tube flow restrictor 106 wherein a mass spectrometer is operated in a chemical ionization mode. The vent restrictor in this case was of 0.25 mm internal diameter and 10 cm long although one skilled in the art would recognize that many different permutations of length of capillary tubing versus internal diameter would work equally as well here for vial venting purposes. In addition, the lower or higher flow capillary may be selected for CI calibration. This may be desired when a high vapor pressure calibrant is used, or when the calibrant is highly electrophilic and calibration is performed in NCI mode.

The relationship of flow to pressure in such restrictors is given by the well-known Poiseuille equation using prior knowledge of the gas viscosity (a function of temperature), restrictor dimensions, and inlet and outlet pressures:

$$\frac{dV}{dT} = \left(\frac{\pi r^4}{16\eta L}\right)\left(\frac{pi^2 - po^2}{po}\right)$$

where: $p_i$=inlet pressure, $p_o$=outlet pressure L is the length of the column $\eta$ is the viscosity of the gas and r is the column internal radius.

Delivery of the calibration vapor is accomplished via controlling the flow of the entrainment gas in general agreement with the above formula. The entrainment gas preferably constitutes air, but may also be selected to include nitrogen, helium or other gasses inert to the calibration compounds.

Flow restrictors 106 and 117 are connected with two inputs 105 and 111 respectively of selector valve 112. In FIG. 1, a "common port" 103 of valve 112 is connected with the "common" port of valve 113. Valve 113 is connected to either the flow restrictors 106 or 117 by valve 112. The output of valve 113 is connected with a main mechanical vacuum roughing pump 114 or it is connected with an ionization chamber 102 of a mass spectrometer 101. In this way, there is a constant flow of calibrant gas either to the ionization region 102 or to the pump 114. This means that the gas delivery apparatus is continuously pseudo-equilibrated and in a pseudo steady state as long as the ionization chamber is evacuated and liquid calibrant sources 109 and 110 are present in vial 123.

Referring to FIG. 1, valve 112 is shown set to deliver the flow from restrictor 117 through valve 113 to the vacuum pump 114. By activating valve 113, as shown by direction arrow 115 where this direction arrow would change to point upward on valve activation, calibrant flowing through the restrictor 117 would be supplied to the ionization chamber 102. With valve 112 set in the opposite direction of the arrow 116 as shown in FIG. 1 (that is, switching valve 112 so that arrow 116 is pointing upwards) calibrant flowing through restrictor 106 would be selectively connected with the ionization chamber 102 or with the vacuum pump 114 depending of the setting of valve 113 (arrow pointing downwards on valve 113 would lead to the vacuum pump and arrow pointing upwards would lead to the ionization chamber).

Valves 112 and 113 are preferably of the three-way type. This allows a continuous flow of calibrant to be maintained through the valves, tubing and related hardware with the final action being delivery of the calibrant to the ion source or diversion of flow to the fore pump. This is desirable, since the actual amount of calibrant delivered may be less than a few tens of nanograms per second. Extremely low amounts of calibrants can have undesirable adsorption-desorption equilibration time requirements. By maintaining continuous flow, these ill effects are substantially eliminated.

In the illustrative embodiment described above having the dimensions of the restrictors described above and the ionization region at about full operating vacuum, the flow rate through the restrictors 106 and 117 was found to be about 0.04 cc/min and about 0.004 cc/min respectively for the permanent entrainment gas (air). In alternative embodiments, a wide range of operating flow rates may be obtained by selecting capillary restrictors with different internal diameters and/or lengths. Air may be prevented from entering capillary tubes 106 and 107 if desired by using an inert gas connected with or flowing across source end 124 of vent restrictor 107. Although FIG. 1 shows vial 123 contained within metering device 100, it may also be connected externally to 100 for example via a threaded connector. This would facilitate refilling of vial 123 with one or more calibrants. In addition, the vial may comprise glass, polycarbonate or other suitably clear material to aid in determining when one of the calibrants is in need of replenishment.

Figure 2:
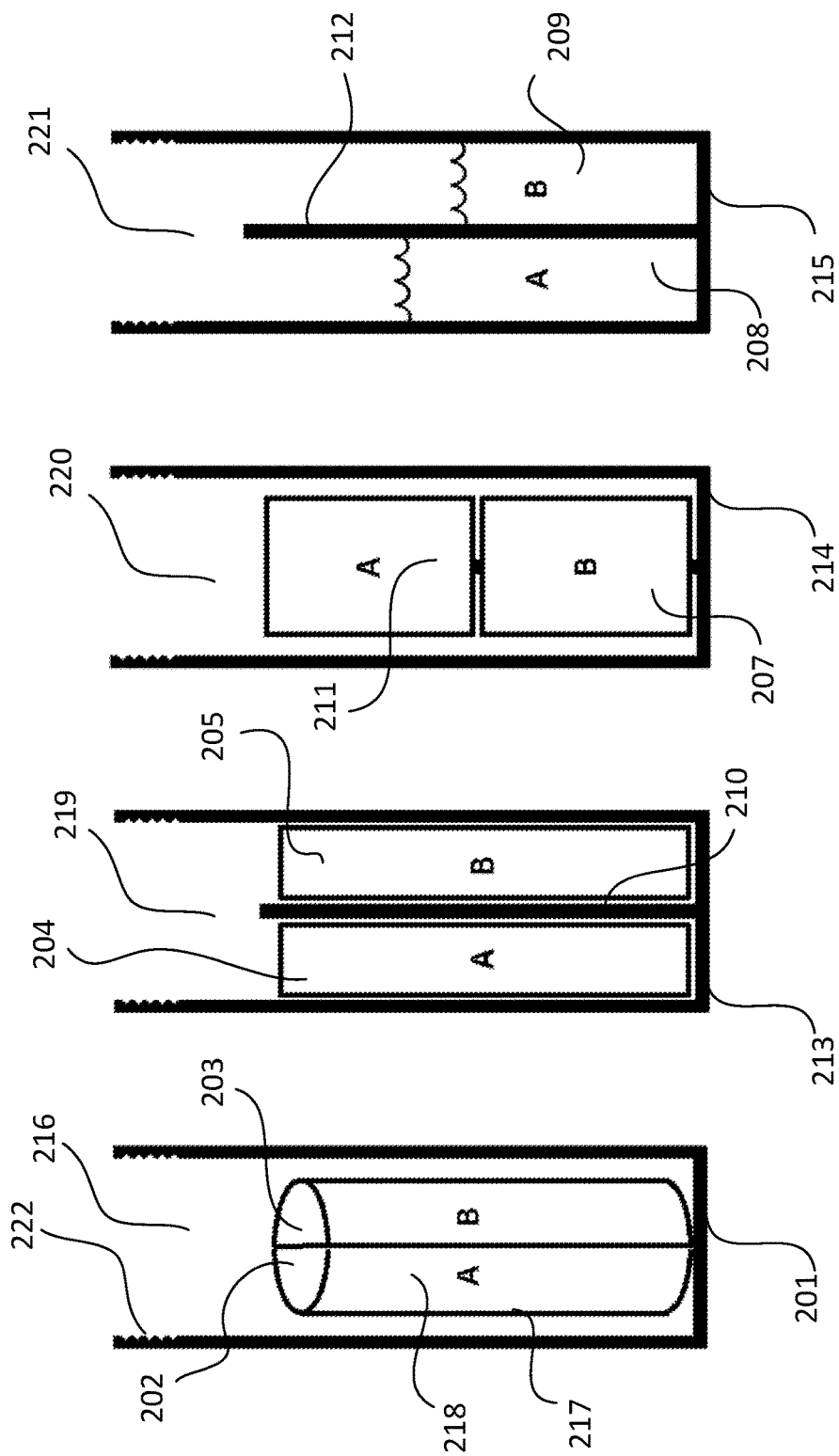
FIG. 2 shows four examples of calibrant vials each holding two different calibrants.

FIG. 2 shows four examples using four different vial configurations for multi-calibrant source vial 123 shown in FIG. 1. Vial 201 contains an inert cylindrical porous vial insert 217 which may be separated into a plurality of distinct sections or contain internal non-porous dividers 218 where each distinct section holds a plurality of different calibrants. As shown in FIG. 2, vial insert 217 is shown specifically split into two distinct sections 202 and 203 for holding liquid calibrants A and B respectively. Vials 201, 213, 214 and 215 may be made from glass or quartz or from a relatively inert polymer, for example, from Delrin® (an acetal homopolymer made by the DuPont Company) or from an inert metal or metal alloy. Insert 217 may be made from any relatively inert porous material such as porous polyethylene.

Vial 213 is shown with an optional vial dividing section 210 which may be centered in the vial or off-set so that the vial may contain, for example, more of calibrant A than calibrant B. Partitions may allow for two or more separate sections in vial 213 which is divided by one or more dividers 210 (one shown). Divider 210 may be inserted into the vial using an inert material or it may be made as part of vial 213. In this embodiment vial 213 may hold calibrants A and B either with or without inert porous inserts. Vial 213 contains inert porous inserts 204 and 205 for holding calibrants A and B respectively.

Vial 214 shows two porous inserts 206 and 207 stacked and holding two calibrants A and B respectively. Again, the inserts may be made of from an inert porous polymer. Vial 215 has a main vial divider that may divide the vial into a plurality of distinct calibrant sections. 215 in FIG. 2 is shown divided into two distinct sections holding liquid calibrants A and B. Again, the divider 212 may be centered or offset as for vial 213 above.

In FIG. 2 the vials are shown with a female threaded upper section 222 which may rotatably engage with a complementary male threaded gas inlet (not shown) on the surface of the metering device of FIG. 1. Many variations are possible to connect the vial to the metering device, for example, by using gas tight quick-fit push-on push-off connectors. The figures herein are not shown to scale, unless a scale coincidently matches a device.

Liquid calibrants should never be allowed to enter any of the calibrant gas capillary tube flow restrictors (for example, 106 and 117 in FIG. 1) nor vent line 124 otherwise these gas lines will become clogged. This would not be a problem with a vertically located vial but if the vial were mounted horizontally, it may present a problem if any liquid in the vials were allowed to make contact with any of the calibrant gas capillary tube flow restrictors. Such restrictors should only ever sample gas vapor from vial headspaces. Liquid calibrants therefore should not be allowed to contact the calibrant gas capillary tube flow restrictors under any circumstances. This can be prevented by not overfilling vials with liquid calibrants and/or using porous glass or polymeric material to hold liquid calibrants.

Figure 3:
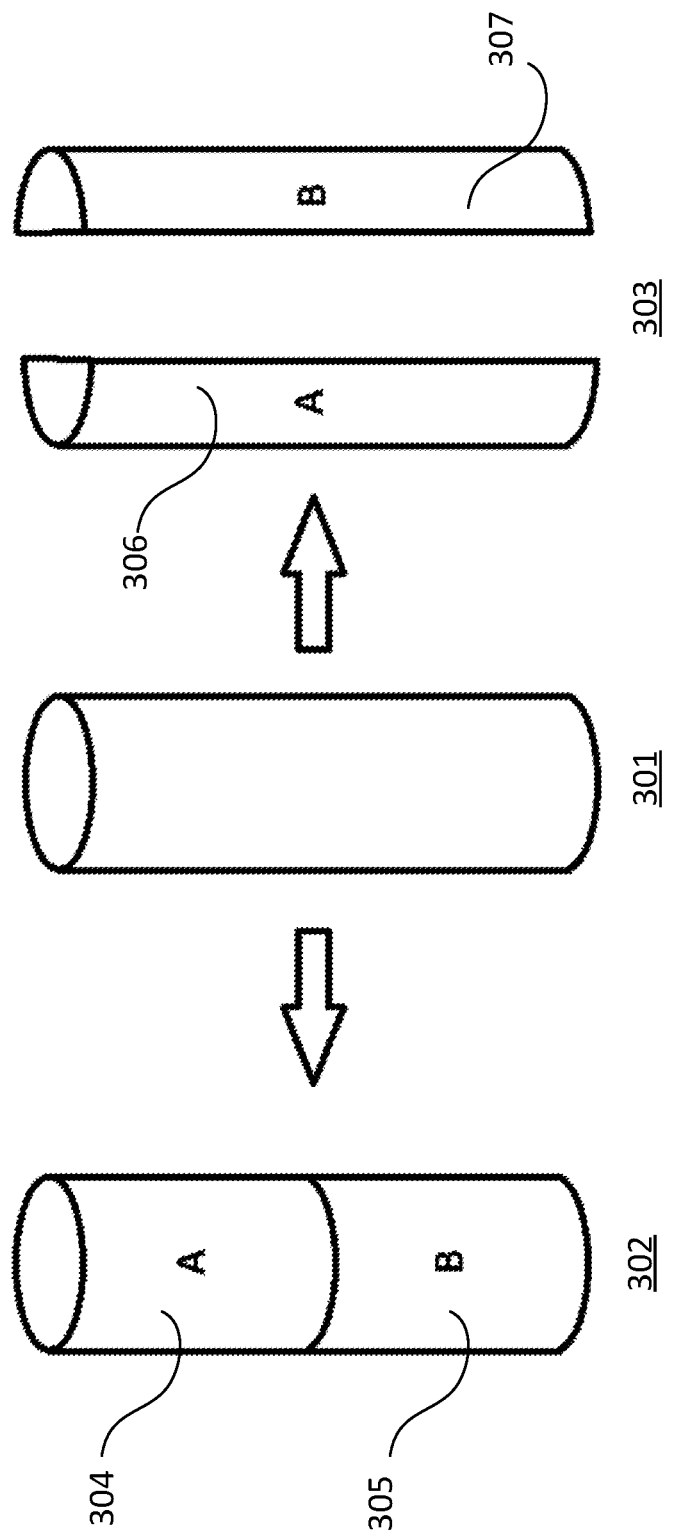
FIG. 3 shows a cylindrical porous calibrant holder being split into two halves in different ways for the purpose of holding two different calibrant materials.

FIG. 3 shows an inert porous vial insert 301 being partitioned in two different ways, radially to give 302 having halves 304 and 305 and axially to give 303 having halves 306 and 307.

Figure 4:
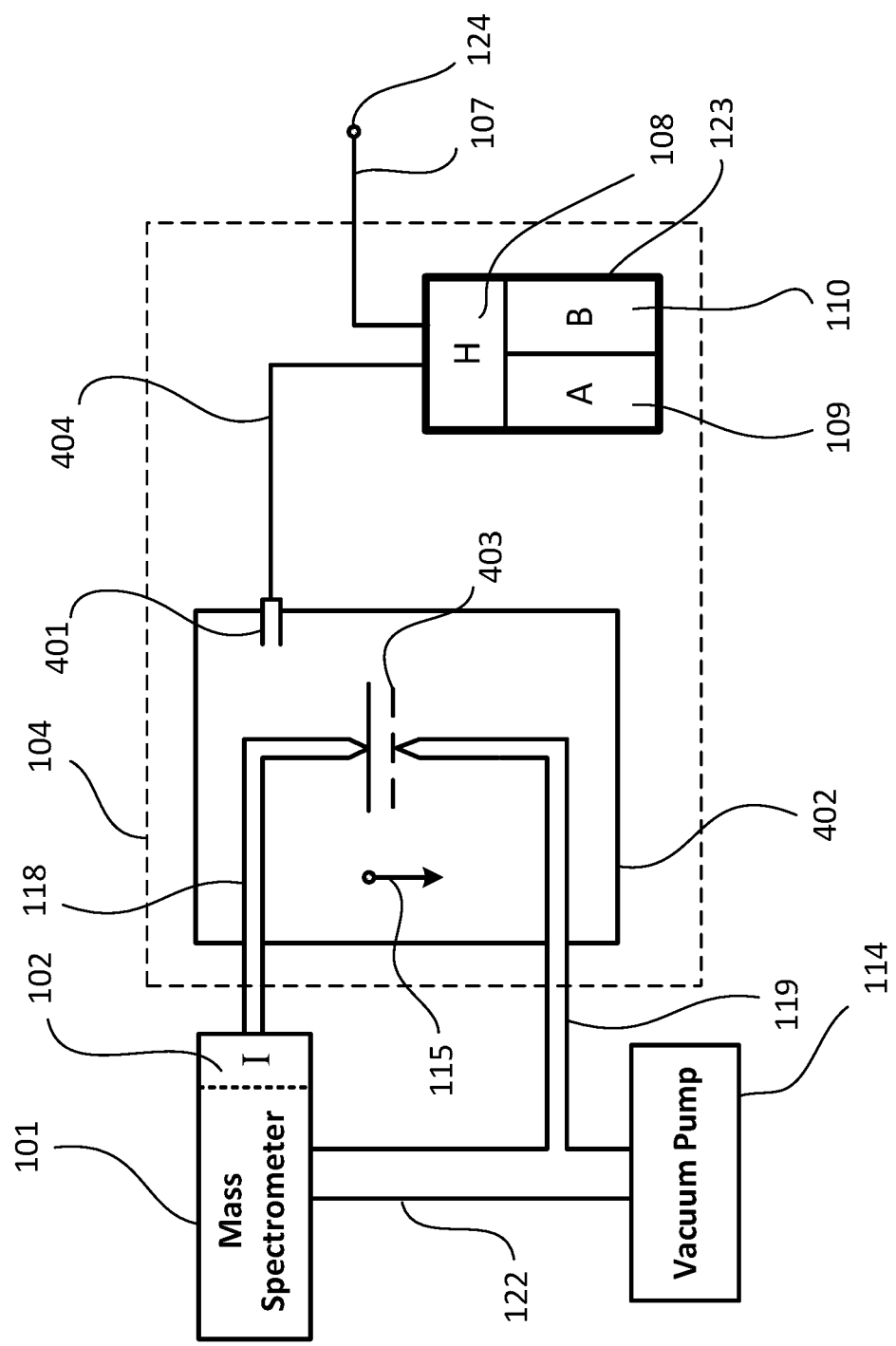
FIG. 4 shows a mass calibration apparatus with two different calibrants, one metering restrictor and one 3-way valve.

FIG. 4 shows an embodiment that has only one 3-way valve 402. This embodiment functions much the same way as the embodiment described in FIG. 1 except that in this case, there is only one calibrant gas capillary tube flow restrictor 404. FIG. 1 describes an embodiment with two calibrant gas capillary tube flow restrictors, 106 and 117. Having only one calibrant gas capillary tube flow restrictor may decrease cost for systems that, for example, do not need chemical ionization, but would like additional ions for EI calibration. A capillary tube having a 0.025 mm internal diameter and 40 cm long may be used for calibrant gas capillary tube flow restrictor 404 with the mass spectrometer operating in electron ionization mode. A 0.050 mm internal diameter and 65 cm long capillary tubing may be used for calibrant gas capillary tube flow restrictor 404 in a mass spectrometer operated in a chemical ionization mode.

Figure 5:
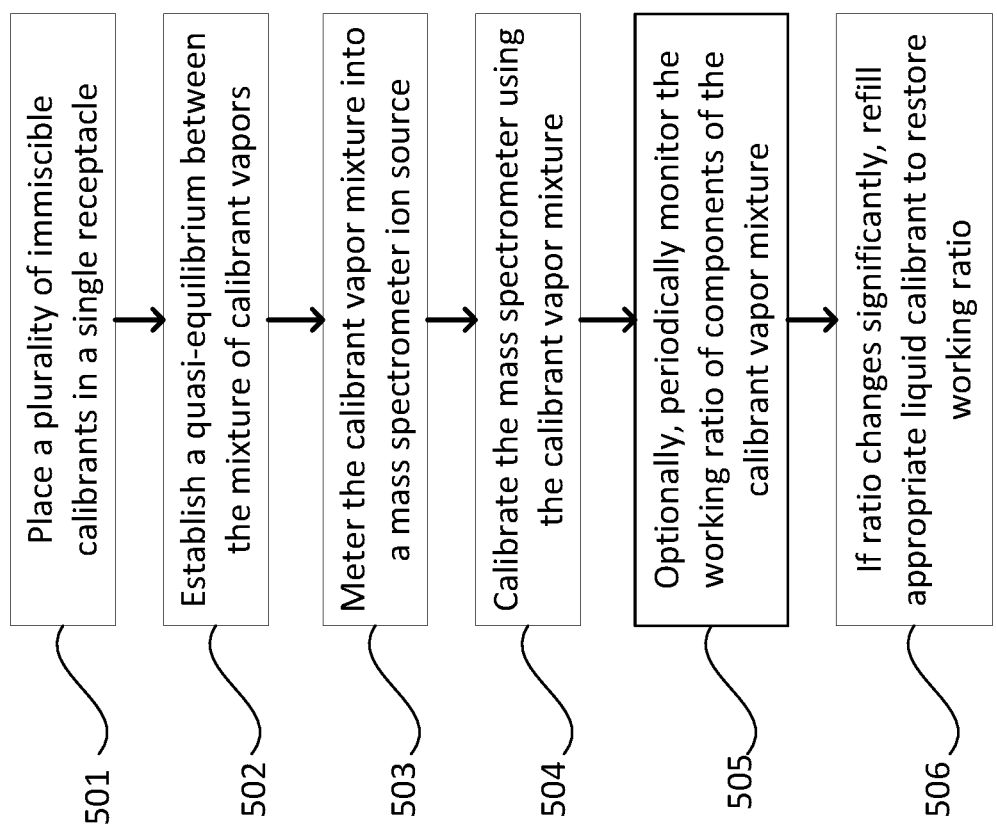
FIG. 5 shows a flowchart where monitoring of a working ratio of different calibrants is periodically performed. A significant change in the working ratio may indicate that one of the calibrants may need to be refilled.

FIG. 5 shows a flowchart that exemplifies an embodiment of the present invention which detects when at least one of the immiscible calibrants needs to be replenished. In this example calibrants are placed in a calibration vial (501) and a quasi-equilibrium calibrant vapor mixture in a common headspace is established (502). The vapor mixture is metered into an ion source of a mass spectrometer (503) and the calibration is performed (504). To detect when at least one of the calibrants requires replenishing, a working ratio of the calibrants is monitored by the mass spectrometer (505). If the working ratio of the calibrants changes significantly as monitored by mass spectrometry, the calibration vial or receptacle may be replenished with any calibrant as necessary to restore the working ratio (506).

Figure 6:
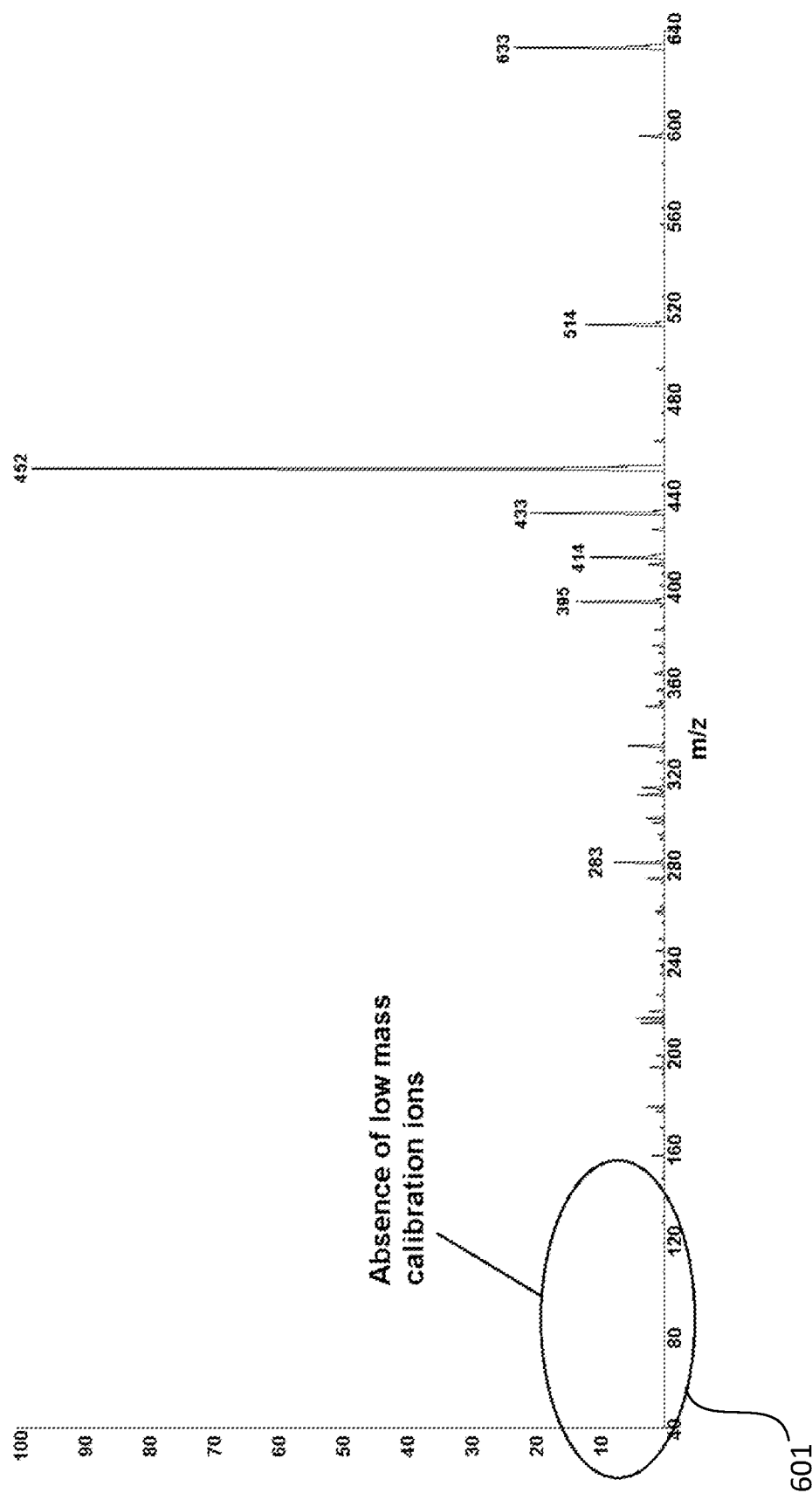
FIG. 6 shows the lack of low mass calibration ions in an exemplary Methane NCI spectrum of perfluorotributylamine.

Referring now to FIG. 6, a prior art exemplary mass spectrum obtained from FC-43 is shown using methane reagent gas in NCI mode. As shown, there is a conspicuous lack of ion formation in the low mass end of the spectrum 601 (around 40 to 150 m/z). Peaks in this area generally can be attributed to impurities in the FC-43.

Figure 7:
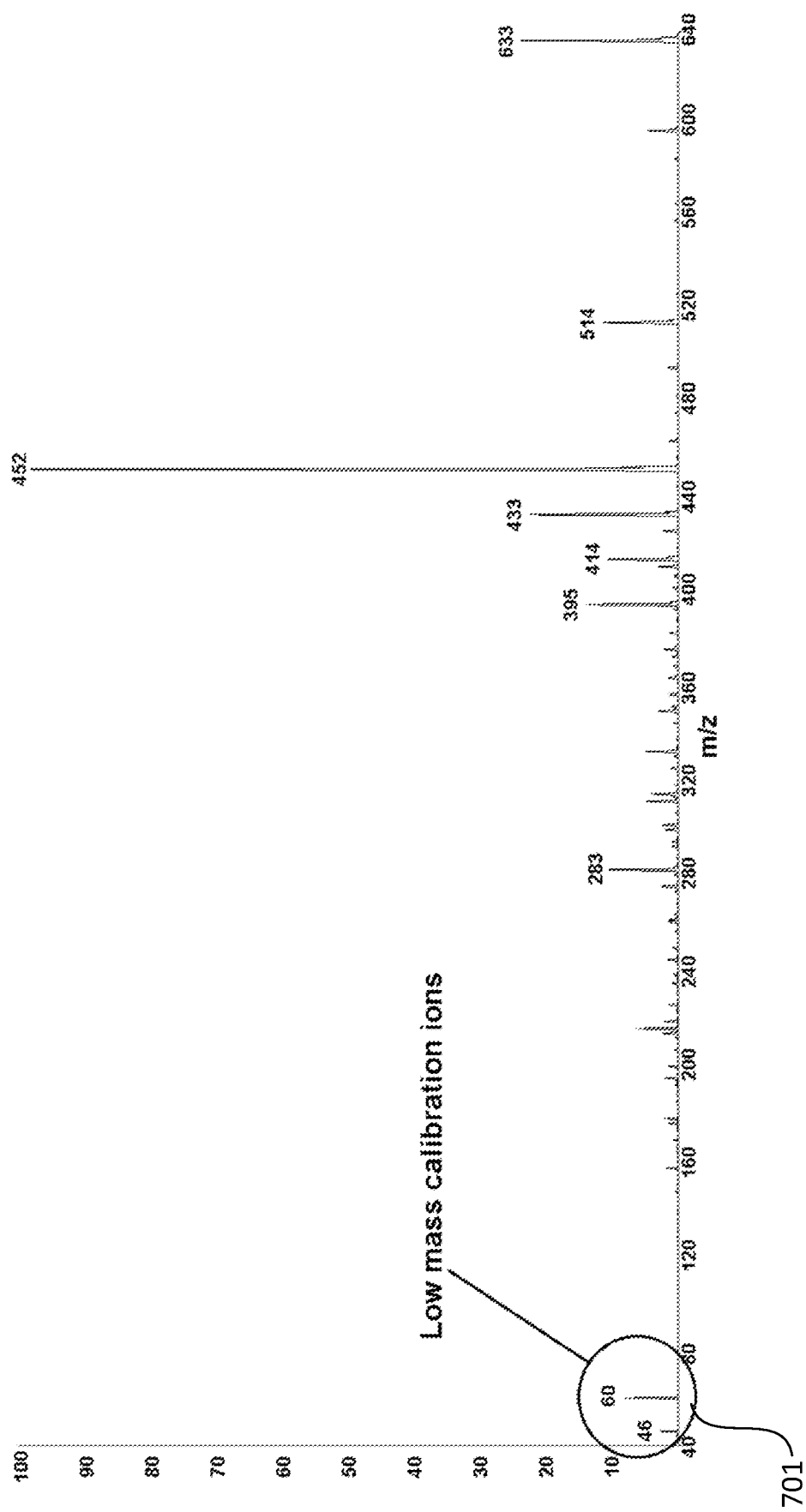
FIG. 7 shows the availability of low mass calibration ions when nitromethane vapor is introduced concurrently with vapor from perfluorotributylamine in Methane NCI mode.

By way of contrast, FIG. 7 illustrates a mass spectrum acquired from a non-limiting embodiment of the present invention wherein approximately 200 uL of nitromethane was absorbed into a porous polyethylene half cylinder A, 218, and approximately 200 uL of FC-43 was absorbed into a porous polyethylene half cylinder B, 203 as in vial 201 as shown in FIG. 2. The employed apparatus was that of FIG. 1. This allowed mass calibration extending down to 60 m/z and/or 46 m/z arising from the formation of negative ions $CH_2NO_2^-$ and $NO_2^-$ ions respectively.

The single calibration vial described above may be replaced by two or more separate calibration vials wherein the two vials are enclosed in a container. In this case a common headspace may be provided within such a container for the one or more separate calibration vials.

The specific embodiments described herein incorporate details to facilitate the understanding of principles of construction and operation of the invention. Such reference herein to specific embodiments and details thereof is not intended to limit the scope of the claims appended hereto. It will be readily apparent to one skilled in the art that various other modifications may be made in the embodiments chosen for illustration without departing from the spirit and scope of the invention as defined by the claims. For example, there are a very large number of molecular positional isomers or other immiscible calibrant compounds that one skilled in the art would recognize that may be substituted for the specific calibrants exemplified herein.

What is claimed is:

1. A gas delivery apparatus for delivering a calibrant gas mixture to an ionization chamber of a mass spectrometer, comprising:
    (a) a plurality of separated liquid calibrants in a calibration receptacle having a common headspace, wherein the calibrant gas mixture forms;
    (b) a vacuum pump operably connected with the mass spectrometer;
    (c) a multiport valve for diverting the calibrant gas mixture in the common headspace to the ionization chamber or to the vacuum pump; and,
    (d) a flow restrictor for metering the calibrant gas mixture from the common headspace to the ionization chamber.

2. The apparatus of claim 1, wherein the flow restrictors are capillary tubes having a preselected internal diameter and length for delivery of the calibrant gas mixture at a desired flow rate.

3. The apparatus of claim 1, wherein the receptacle contains a venting flow restrictor, vented to atmosphere or vented to a source of inert gas.

4. A gas delivery apparatus as in claim 1 wherein there is a constant flow of the calibrant gas mixture either to the ionization chamber or the vacuum pump.

5. A gas delivery apparatus as in claim 1 wherein the calibrant gas mixture in the headspace is continuously equilibrated.

6. The apparatus of claim 5, wherein a ratio of calibrant gas vapors in the headspace is periodically monitored, whereby any significant change in the ratio over time indicates that at least one of the liquid calibrants needs to be replenished.

7. The apparatus of claim 1, wherein the separated liquid calibrants are immiscible liquids.

8. The apparatus of claim 1, wherein at least one of the separate liquid calibrants is a triperfluoroalkyl tertiary amine.

9. The apparatus of claim 1, wherein at least one of the separated liquid calibrants contains perfluoroalkyl groups.

10. The apparatus of claim 1, wherein the plurality of separated liquid calibrants are individually absorbed into one or more inert porous solid materials within the receptacle.

11. The apparatus of claim 1, wherein at least two calibration receptacles are used, wherein each calibration receptacle holds at least one liquid calibrant and wherein all of the calibration receptacles have common headspace.

12. A gas delivery apparatus for delivering a mixture of calibrant gases to an ionization chamber of a mass spectrometer, comprising:
    (a) a plurality of separated liquid calibrants in a calibration receptacle having a common headspace, wherein a calibrant gas mixture forms;
    (b) a vacuum pump operably connected with the mass spectrometer;
    (c) a multiport valve for connecting the calibrant gas mixture in the common headspace with the ionization chamber or with the vacuum pump;
    (d) a first flow restrictor and a second flow restrictor for metering the calibrant gas mixture from the common headspace to a second valve with a first flow rate or with a second flow rate respectively; and,
    (e) wherein the second valve connects the first or second flow restrictor with the first valve.

13. A method of delivering a calibrant gas mixture to an ionization chamber of a mass spectrometer, comprising:
    (a) providing a plurality of separated immiscible liquid calibrants in a calibration vial;
    (b) maintaining a quasi-equilibrium composition of the calibrant gas mixture in a headspace of the calibration vial; and,
    (c) allowing the calibrant gas mixture into either the ionization chamber of the mass spectrometer or routing it to a vacuum pump.

14. The method of claim 13, wherein a second flow restrictor of different length or internal diameter or both is connected between the receptacle and the multiport valve and configured to meter a different quantity of the calibrant gas mixture at a different flow rate out of the receptacle and into the ionization chamber.

* * * * *

UNITED STATES PATENT AND TRADEMARK OFFICE
CERTIFICATE OF CORRECTION

PATENT NO. : 10,600,626 B1  
APPLICATION NO. : 16/220291  
DATED : March 24, 2020  
INVENTOR(S) : Jason S. Cole et al.

Page 1 of 1

It is certified that error appears in the above-identified patent and that said Letters Patent is hereby corrected as shown below:

On the Title Page

Under item (73) Assignee:  
Replace "THERMOS FINNIGAN LLC"  
With --THERMO FINNIGAN LLC--

Signed and Sealed this  
Eighth Day of September, 2020

Andrei Iancu  
*Director of the United States Patent and Trademark Office*